(12) United States Patent
Fujita et al.

(10) Patent No.: US 7,795,034 B2
(45) Date of Patent: Sep. 14, 2010

(54) SPECIFIC COMPONENT MEASURING METHOD BY SPECTRAL MEASUREMENT

(75) Inventors: Takashi Fujita, Hyogo (JP); Sachiko Yamamoto, Hyogo (JP); Hiroyuki Yamada, Hyogo (JP); Wataru Akahane, Hyogo (JP)

(73) Assignee: Wako Pure Chemical Industries, Ltd., Osaka-shi (JP)

( * ) Notice: Subject to any disclaimer, the term of this patent is extended or adjusted under 35 U.S.C. 154(b) by 867 days.

(21) Appl. No.: 10/561,538

(22) PCT Filed: Jun. 21, 2004

(86) PCT No.: PCT/JP2004/008711

§ 371 (c)(1),
(2), (4) Date: Dec. 19, 2005

(87) PCT Pub. No.: WO2005/003744

PCT Pub. Date: Jan. 13, 2005

(65) Prior Publication Data

US 2006/0170914 A1     Aug. 3, 2006

(30) Foreign Application Priority Data

Jul. 3, 2003   (JP) .............................. 2003-270797
Mar. 31, 2004  (JP) .............................. 2004-106577

(51) Int. Cl.
*G01N 25/18* (2006.01)

(52) U.S. Cl. .................. 436/149; 356/311; 422/52; 430/527; 430/530

(58) Field of Classification Search ................ 436/149; 356/311; 422/52; 430/527, 530
See application file for complete search history.

(56) References Cited

U.S. PATENT DOCUMENTS 5,898,559 A * 4/1999 Smith .......................... 361/215

(Continued)

FOREIGN PATENT DOCUMENTS

JP     6-18968     3/1994

(Continued)

OTHER PUBLICATIONS

Castranova, Vincent, et al., Augmentation of Pulmonary Reactions to Quartz Inhalation by trace amounts of iron-containing particles, 1997, Environmental Health Perspective 105, Supplement 5, retreived online at http://www.ehponline.org/members/1997/Suppl-5/castranova-full.html.*

(Continued)

*Primary Examiner*—Yelena G Gakh
*Assistant Examiner*—Robert Xu
(74) *Attorney, Agent, or Firm*—Westerman, Hattori, Daniels & Adrian, LLP

(57) ABSTRACT

The present invention discloses a method for measuring an amount of an objective component to be measured in a sample, which comprises; preventing an electric charge in an atmosphere in a photometry chamber from transferring to the surface of a solution which generates light due to an energy variation of a substance induced by the objective component in the sample, measuring value of the light, and determining an amount of the objective component in the sample on the basis of the measured value thus obtained, and an instrument used for the method.

According to the present invention, in measurement of an objective component in a sample using a spectrophotometer, problems such as between-day variation of signal values or increase of background value, etc. can be solved, and a trace component can be measured in high accuracy and high sensitivity.

6 Claims, 1 Drawing Sheet

U.S. PATENT DOCUMENTS

| | | | | |
|---|---|---|---|---|
| 6,144,448 | A | * | 11/2000 | Mitoma ........................ 356/317 |
| 6,290,868 | B1 | * | 9/2001 | Martin et al. ............. 252/62.54 |
| 6,602,464 | B1 | * | 8/2003 | Rapp et al. ...................... 422/5 |
| 2001/0038450 | A1 | * | 11/2001 | McCaffrey et al. ........... 356/311 |

FOREIGN PATENT DOCUMENTS

| JP | 10-127268 A | 5/1998 |
|---|---|---|
| JP | 2003-344276 A | 12/2003 |

OTHER PUBLICATIONS

Ryoji, Miyasato, Prevention of product troubles by static electricity failure. Static electricity removal and static elimination materials. Development cases of static elimination materials. Persistant static elimination ABS resins "Novalloy E series", 1999, Engineering Materials, vol. 47(11), pp. 38-41.(only attached English Title and abstract).*

Notification of Transmittal of Translation of the International Preliminary Report on Patentability (Form PCT/IB/338) of International Application No. PCT/JP2004/008711 mailed Jun. 1, 2006 with Forms PCT/IB/373 and PCT/ISA/237.

Ryoji (Engineering Materials, vol. 47(11), pp. 38-41)—Complete Document and Full English Translation, 1999.

Japanese Office Action dispatched May 25, 2010, for corresponding Japanese Patent Application No. 2005-511319.

* cited by examiner

SPECIFIC COMPONENT MEASURING METHOD BY SPECTRAL MEASUREMENT

TECHNICAL FIELD

The present invention relates to a method for measuring a trace component in a sample originated from a living body such as serum, plasma, or the like using a measuring instrument. In particular, the present invention relates to a method for quantifying an objective component to be measured in high accuracy by preventing influences such as measurement errors or increased background value caused by localized electric charge in measuring environment, especially in an atmosphere surrounding a reaction vessel, while measuring luminescence, fluorescence, phosphorescence, or the like using a spectrophotometer, and an instrument used for the method.

BACKGROUND ART

Analysis and/or measurement of an objective component to be measured by measuring luminescence, fluorescence, phosphorescence or the like have been widely utilized especially for the measurement of trace components such as environmental hormones or in vivo substances, because of its high sensitivity. In such highly sensitive spectrophotometry, small signal variation is required.

However, there is a problem of inability of correct measurement. Because a photodetector used for such high sensitive spectrophotometry is so sensitive, the photodetector detects even weak signals irrelevant to the objective measurement. As a method for preventing such measurement errors caused by weak signals irrelevant to the objective measurement, for example, a method for avoiding the influence of incorrect electric current by grounding of the photoelectric converter, or a method for detecting only objective signals by subtracting incorrect current measured in advance has been employed.

However, even though these procedures are performed, problems which are disturbed the high-accuracy measurement of the objective component remains, since background value varies by each measurement. Therefore, correct values cannot be obtained unless a calibration curve showing the relationship between the signal values and the concentrations of the objective component obtained by measuring the signal value using standard of the objective component containing known concentrations as a sample is established for each measurement.

For example, when a trace component is determined by using a luminescence property of luminol, luminol is oxidized by an action of appropriate amount of an oxidase such as peroxidase (POD) in accordance with the amount of the objective component to be measured in the presence of hydrogen peroxide, and fluorescence is generated (emit light). However, even when the concentration of the objective component is zero and the oxidase such as POD is not present, luminol is oxidized and generates luminescence slightly. There are problems which these energy variation value (background value) of luminol caused by factors other than the oxidase such as POD, or energy variation value generated by the oxidase such as POD (they are often referred to collectively as "signal value"), are varied significantly by change in measurement environment such as day and time of measurement, measurement place, and the like.

Such phenomena as mentioned above are generally observed in a method for measuring a signal value of energy variation of a substance such as luminescence, fluorescence, phosphorescence, and thus posing problems.

Therefore, development of a measuring method which provides low variation of the signal values and an instrument used for the method has been desired.

DISCLOSURE OF THE INVENTION

Problem To Be Solved By The Invention

The present invention has been accomplished in view of such circumstances as above, and an object of the present invention is to provide a method for measuring an objective component to be measured in high accuracy, reproducibility and simplicity, wherein the measurement of an objective component in a sample using a spectrophotometer is performed by suppressing or reducing a influence of electric charge in an atmosphere surrounding a reaction vessel which is occurred in measuring environment, and to provide an instrument used for the method.

Means For Solving Problems

The present invention was accomplished to solve the above-described problems, and consists of the following;

(1) A method for measuring an amount of an objective component to be measured in a sample, which comprises;
preventing an electric charge in an atmosphere in a photometry chamber from transferring to the surface of a solution which generates light due to an energy variation of a substance induced by the objective component in the sample,
measuring value of the light, and
determining an amount of the objective component in the sample on the basis of the measured value thus obtained.

(2) A method for measuring an amount of an objective component to be measured in a sample, which comprises; making an atmosphere surrounding a reaction vessel and/or a reaction vessel in a photometry chamber electrically constant, measuring value of light generated due to an energy variation of a substance induced by the objective component in the sample in the reaction vessel in the photometry chamber, and determining an amount of the objective component in the sample on the basis of the measured value thus obtained.

(3) An instrument for measuring value of light generated due to an energy variation of a substance in a solution instrument, which contains a mechanism for measuring value of light generated due to an energy variation of a substance in a solution and a mechanism for preventing an electric charge in an atmosphere in a photometry chamber from transferring to the surface of the solution.

(4) An instrument for measuring value of light generated due to an energy variation of a substance, which contains a mechanism for measuring value of light generated due to an energy variation of a substance and a mechanism for treating for making an atmosphere surrounding a reaction vessel and/or a reaction vessel of a photometry chamber electrically constant.

Namely, the present inventors have studied extensively in order to find out a method for measuring an objective component to be measured such as a trace component to be measured in high accuracy, by suppressing or avoiding influences of variation of the signal value in spectrophotoscopic measurement using a spectrophotometer, etc. As the result, the present inventors have found that the variation of the signal value can be suppressed by preventing an electric charge in an atmosphere in a photometry chamber from transferring to the surface of the solution which generates light due to the energy variation of a substance induced by the objective component in the sample, and the present invention has been accomplished.

A measuring method of the present invention is a method for measuring an amount of an objective component to be measured in a sample, which comprises; preventing an electric charge in an atmosphere in a photometry chamber from transferring to the surface of a solution which generates light due to an energy variation of a substance induced by the objective component in the sample, measuring value of the light, and determining an amount of the objective component in the sample on the basis of the measured value thus obtained.

In the measuring method of the present invention, the method for preventing an electric charge in an atmosphere in a photometry chamber from transferring to the surface of a solution which generates light due to the energy variation of a substance induced by the objective component in the sample includes, for example, a method for making an atmosphere surrounding a reaction vessel and/or an atmosphere surrounding the reaction vessel in the photometry chamber electrically constant, or a method for blocking a contact of the atmosphere in the photometry chamber with the solution in the reaction vessel.

The atmosphere surrounding a reaction vessel and/or the atmosphere surrounding a reaction vessel in a photometry chamber is defined as air with which the reaction vessel in the photometry chamber contacts, or air in the photometry chamber equipped in the spectrophotometer.

Light generated by the energy variation of the substance induced by the objective component in the sample of the present invention, includes luminescence, fluorescence or phosphorescence.

In the present invention, the spectrophotometry denotes to measure light intensity distribution in spectrum of luminescence, fluorescence, phosphorescence, and the like. The photodetector includes for example, but not limited to, a photodiode, a photoelectron multiplier and a CCD camera. An output method includes, for example, but not limited to, a photocounting method, a current-output method and a voltage-output method.

The spectrophotometer used in the present invention is not specifically limited and includes all of those generally used in this field such as one equipped with only a spectroscopic function; one equipped with both reagent dispensing function and the spectroscopic function; or a automated analyzer having a reagent dispensing function, a B/F separating function and the spectroscopic function all together. Specific examples of such a spectrophotometer includes Safire™ (Tecan Co., Ltd.) for having only the spectroscopic function; LB953 (Berthold Technologies Co., Ltd.) for having both the reagent dispensing function and the spectroscopic function; an Automated Chemiluminescence Enzyme Immunoassay Analyzer such as SphereLight 180 (Olympus Co., Ltd.) for the automated analyzer.

The photometry chamber in the present invention denotes a space equipped with the photodetector in the spectrophotometer where a sample (the reaction vessel) is set when light is actually measured.

As the reaction vessel in the present invention, various kinds of vessels can be used, and it is not particularly limited as long as it is applicable to the spectrophotometer to be used, and includes, for example, one made from glass or plastic such as polypropylene or polystyrene. A vessel exclusive for the spectrophotometer can also be used. In addition, there is a cartridge type vessel for the automated analyzer having plural concave portions (referred to as a reaction bath or a reagent cell) in which a solution will be dispensed. This type of vessel can also be used in the present invention.

In the present invention, "to make the atmosphere surrounding the reaction vessel and/or the atmosphere surrounding the reaction vessel in the photometry chamber electrically constant" means that either the example in which electric charge of the electrical environment in the atmosphere surrounding the reaction vessel and/or the atmosphere surrounding the reaction vessel in the photometry chamber is neutralized; the bias of electric charge of the electrical environment is suppressed; or an electric charge of the electrical environment is made constant. The treatment is performed at just before and/or at spectrometric measurement time, through spectrometric measurement time, or through from just before the measurement time to the measurement time.

The method for making the atmosphere surrounding the reaction vessel and/or the atmosphere surrounding the reaction vessel in the photometry chamber electrically constant is not particularly limited, as long as it can achieve this purpose, and includes, for example, a method for treating the atmosphere surrounding the reaction vessel and/or the atmosphere surrounding the reaction vessel in the photometry chamber by using one or more of material selected from the group consisting of; (1) gas having a constant electric charge, (2) an neutralization apparatus, or (3) a material having a static electricity elimination effect.

Gas having a constant electric charge in the present invention are not particularly limited as long as they are gas having no electric charge or having a constant electric charge by itself and no adverse influence on the spectrophotometry, and includes, for example, commercially available cylinder contained air, or an inert gas such as nitrogen, argon or helium. Also, air from outside environment surrounding the measuring instrument or other gas supplied by using publicly known equipment such as a compressor or a pump; and ionized gas supplied, for example, by an ionizer also. From the viewpoint of safety, hygiene and efficiency of gas exchange in the reaction vessel, gas such as air, nitrogen or argon are preferable. Further, from the aspects of easiness of use and economy, to use air in outside environment surrounding the spectrophotometer is preferable.

An equipment for supplying the gas are not particularly limited as long as they can supply the gas to an objective site. This includes publicly known equipment such as an ionizer, a high-pressure steel cylinder, a compressor or a pump, and an air pipe to be connected with the equipment for introducing the gas toward the objective site.

Preferred examples of the ionizer are not particularly limited as long as they are equipments providing, for example, a unit of a discharge electrode which generates a positive or a negative ion, and a unit of a discharge tube which releases a positive or a negative ion. For example, commercially available equipments such as an ionizer or an ion blower can be utilized.

When a case that a gas is supplied by the pump in the present invention, for example, a piston pump can be used.

The neutralization apparatus in the present invention may be a static charge eliminator which can neutralize an electric charge from the atmosphere surrounding the reaction vessel and/or the atmosphere surrounding the reaction vessel in the photometry chamber by generating, for example, both positive and negative ions from electric discharge part. And the neutralization apparatus may have acceptable size to be installed in a spectrophotometer. For example, a superimposed voltage type neutralization apparatus such as an alternating-current neutralization apparatus, and a self-discharge type neutralization apparatus which discharges electricity by concentrating electric field at an electrode tip of the neutralization apparatus according to electric potential of a charged body are also included. In addition, the neutralization apparatus may be any one of a direct-current type or an alternating-current type, and a bar type or a blow type. For example, a commercially available static charge eliminator (e.g., SJ010 SJ020, Keyence Corporation) may be used.

As the material having a static electricity elimination effect in the present invention, a sheet having a static electricity elimination effect (hereinafter abbreviate as "an anti-static sheet") such as a tape having a static electricity elimination effect (hereinafter abbreviate as "an anti-static tape") (e.g. "tape anti-static" Japan Vilene Company) may be applied. For example, a material which contains an electric conducting layer and its supporter as a constituent, and more specifically the material described in JP-A 5-174991, JP-A7-243174, JP-A5-263318 and JP-A 6-215854 are included.

In more detail, the supporter of the electric conducting layer includes, entangled nonwoven fabrics, fabrics or knits composed of natural fibers such as silk, wool, cotton, flax; regenerated fibers such as rayon fiber; semi-synthetic fibers such as acetate fiber; synthetic fibers containing one component such as polyamide fiber, polyvinyl alcohol fiber, acrylic fiber, polyester fiber, polyvinyliden chloride fiber, polyvinyl chloride fiber, polyurethane fiber, polyethylene fiber, polypropylene fiber; and composite fibers of the core-in-shell type, or the side by side type containing two or more components.

A component of the electric conducting layer includes polymers produced by polymerization of a monomer such as acetylene, benzene, aniline, phenylacetylene, pyrrole, furan, thiophene, indole and their derivatives. These polymers may be processed with an electrically conductive substance (for example, a metal such as stainless steel, aluminum, zinc, cupper, tin and silver, or carbon) before or after coating over the above-mentioned supporter. The above-mentioned supporter is coated almost totally with these polymers to form the electric conducting layer.

Further, the anti-static sheet preferably has a non-conducting layer. For example, the sheet having an adhesive layer on the supporter so that it is attached at the right position for carrying out an elimination of static electricity is preferable. Typically, the adhesive layer composed of, for example, thermoplastic synthetic resins such as homopolymers or copolymers derived from such a monomer as an acrylic ester, vinyl acetate, vinyl chloride, vinylidene chloride, an acrylic monomer, styrene and an olefin; rubber such as natural rubber, natural-synthetic rubber, nitrile rubber, styrene-butadiene rubber, chloroprene rubber, butyl rubber; or thermosetting resins such as an urea-formalin resin, a melanin-formalin resin and a phenolic resin may be formed.

More typically, the sheet having a static electricity elimination effect includes, for example, but not limited to, a anti-static sheet having an entangled nonwoven fabric which is coated almost as a whole with an electron conjugated polymer, and that is formed an electric conducting layer having a higher electric conductivity than the electron conjugated polymer (JP-A 5-174991), an ant-static sheet composed of a fiber sheet of synthetic rubber and/or elastomer as a main component in which the surface is coated with an electron conjugated polymer (JP-A7-243174), and a cloth having a static electricity elimination effect which woven with conductive composite fibers composed of a protective polymer layer, a covering polymer layer and an electric conducting layer (JP-A 5-263318). In addition, sheet substances formed with conductive fibers such as metal plated conductive fiber, metal fiber, carbon fiber, metallic ion containing fiber, and sheet substance obtained by fiber sheet formulation using such as regenerated fiber, semi-synthetic fiber, synthetic fiber, inorganic fiber, plant fiber, animal fiber and mineral fiber, followed by furnishing conductivity (JP-A 6-215854).

In the present invention, the above-mentioned methods (1), (2) and (3) may be used alone or in arbitrary combination.

More detailed explanation for each procedure is given below.

(1) A Method for Treating with Gas Having a Constant Electric Charge

A typical example of the method includes, for example, (i) a method for blowing more than a certain amount of gas having a constant electric charge to the reaction vessel, (ii) a method for exchanging the atmosphere in the photometry chamber with gas having a constant electric charge by circulating gas having a constant electric charge.

As to the method (i), when an automated analyzer is utilized, for example, a gas circulation pipe led from an equipment for supplying the gas having a constant electric charge (e.g. a pump, or an ionizer) is installed in the former position of the photometry chamber to where the reaction vessel of the analyzer is moved, and the gas may be blown to the reaction vessel at a stage before the reaction vessel is moved to the photometry chamber.

Further, such procedure may be set up as to blow gas having a constant electric charge to the reaction vessel every time when the reaction vessel passes through in front of the gas circulation pipe. When the automatic analyzer is set to allow the gas to circulate in such area continuously during spectrophotometric measurement, the above-mentioned set up of blowing schedule can be eliminated.

When a sample prepared by manual means is subjected to the measurement using a spectrophotometer, the reaction vessel may be blown by gas having a constant electric charge, and then the reaction vessel may be set to the photometric area.

As to the method (ii), for example, when an automated analyzer is utilized, the method described below is included as an example. That is, a gas circulation pipe led from an equipment for supplying the gas having a constant electric charge (e.g. a pump, or an ionizer) is installed in the automated analyzer, and makes the gas flow in the photometry chamber. In this regard, since the photometry chamber has to be light shielded, the gas circulation pipe is set in former position of the photometry chamber rather than in the photometry chamber, and allows the gas flow toward the photometry chamber during the measurement. And when the reaction vessel in which a sample and reagents are held is moved to the photometry chamber and a shielding board is opened, the gas is supplied to the photometry chamber through the gas circulation pipe, followed by closing the shielding board, and thus light shielding of the photometry chamber may be maintained. So, this method is preferable.

Alternatively, gas may be flowed in every time when the shielding board opens. When the gas is kept flowing continuously during the photometric measurement, it is not necessary to rely on such complicated set up as gas flowing at every opening time of the shielding board.

When a sample prepared by manual means is subjected to the measurement using a spectrophotometer, the gas circulation pipe led from an equipment for supplying the gas having a constant electric charge is set up to the around of the photometry chamber, similarly as in an automated analyzer, and the gas may be blown to the photometric area through the gas pipe.

In case where the method (i) is enforced, the amount and strength (flow rate) of the gas having a constant electric charge to be blown to the reaction vessel may be such level as sufficient to remove an electric charge of the reaction vessel. In case where the method (ii) is enforced, the amount and flow rate of gas having a constant electric charge to be circulated to the photometric area may be set to be able to introduce the sufficient amount of gas to exchange gas in the objective photometry chamber by the gas.

(2) Method For Using A Neutralization Apparatus

As to a typical example of the method, when an automated analyzer is utilized, for example, a neutralization apparatus is installed in just former position to where the reaction vessel of the analyzer is moved into the photometry chamber, and the reaction vessel can be passed through the effective area of the neutralization apparatus (charge neutralization area) at a stage before the reaction vessel is moved into the photometry chamber.

When the above method is enforced, such a procedure may be adopted as the reaction vessel is subjected to ion exposure every time when each reaction vessel set on a turning table passes in front of the ion-discharging site of the neutralization apparatus. When the neutralization apparatus is set to work throughout the spectrophotometric measurement to allow the reaction vessels come serially into the charge neutralization area one after another, the above-mentioned set up for charge neutralization program is not required.

For enforcement of the method, the amount of ion exposure to the reaction vessel may be required at such level as sufficient to neutralize electric charge of the reaction vessel.

(3) A Method for Using Material Having a Static Electricity Elimination Effect As for the method, there is, for example, a method for attaching a material having a static electricity elimination effect to an inside wall surface of a photometric camber (e.g. an anti-static sheet). The anti-static sheet may be attached to any place in the photometry chamber unless the measurement operation is disturbed. Also, the size of the anti-static sheet is not especially limited, as long as it is not too large without additional effect and uneconomical. In addition, it is not necessary to attach the sheet all-around the inside wall surface of the photometry chamber. When the volume of the photometry chamber is about 4 cm×3 cm×8 cm, belt-like attachment on the inside wall surface by a tape-shaped one having 2 to 3 cm width may be sufficient.

In addition, in the case of the reaction vessel is a cartridge type, the ant-static sheet may be attached along the outside of the cartridge. The anti-static sheet may also be attached both along the outside of the cartridge and inside wall surface of the photometry chamber. In particular, to attach the anti-static sheet at the position where the cartridge is sandwiched between both sides is effective. Typically, this includes, for example, (i) a method for attaching an anti-static sheet on the inside wall surface of the photometry chamber parallel to the longitudinal side surface of the cartridge, (ii) a method for attaching an anti-static sheet on the longitudinal outside surface of the cartridge, and (iii) a method for carrying out both methods (i) and (ii).

Among the above three treatment methods (1) to (3), the method (3) of using material having a static electricity elimination effect is the simplest procedure.

Also, the method for blowing gas having a constant electric charge to the reaction vessel at the stage before the reaction vessel is moved to the photometry chamber, or the method for using the neutralization apparatus is also simple and preferable procedure.

In the present invention, as "a method for blocking a contact of the atmosphere in the photometry chamber with the solution in the reaction vessel" includes, for example, (1) a method for shutting an opening part of the reaction vessel holding the solution which generates light due to the energy variation of the substance induced by the objective component in the sample with a sheet, or (2) a method for covering the surface of the solution in the reaction vessel with a substance insoluble to the solution.

In the method (1) for shutting the opening part of the reaction vessel holding the solution with a sheet includes, for example, a method for shutting the opening part of the reaction vessel holding the solution with a sheet such as a cellophane tape, an aluminum seal, an aluminum foil, a paper tape or a plastic tape and the like which can block a contact of the atmosphere in the photometry chamber with the solution in the reaction vessel. In so doing, it is preferable to shut whole of the opening parts by sealing to prevent leaking of the atmosphere in the reaction vessel to outside of it, but complete seal is not essential.

Preferable embodiments of the reaction vessel in which the solution is held are described above.

The method (2) for covering the surface of the solution which generates light due to energy variation of the substance induced by the objective component in the sample with a substance insoluble in the solution in the reaction vessel includes, (i) a method for blocking the contact of the atmosphere in the photometry chamber with the solution in the reaction vessel by covering the surface of the solution with liquid which is insoluble in the solution in the reaction vessel, and the liquid has a property of spreading over the surface of the solution in the vessel, and (ii) a method for blocking a contact of the atmosphere in the photometry chamber with the solution in the reaction vessel by covering the surface of the solution by applying (floating) a substance which has lower specific gravity than the solution in the reaction vessel and is insoluble in the solution and has a property of floating on the surface of the solution.

The liquid which is insoluble in the solution in the reaction vessel, and having the property of spreading over the surface of the solution in the vessel used in the method (i) includes, for example, silicon oil, hexane and liquid paraffin, etc. when the solution in the reaction vessel is an aqueous solution, but not limited thereto. When the solution in the reaction vessel is non-aqueous solution, the liquid includes, for example, hexane and benzene, but not limited thereto.

The substance which has lower specific gravity than the solution in the reaction vessel and is insoluble in the solution and has a property of floating on the surface of the solution used in the method (ii) includes, for example, cork and polystyrene foam, but not limited thereto.

The method for measuring an amount of the objective component in the sample of the present invention may be performed by measuring the energy variation of a substance induced by the presence of the objective component in the sample, for example, luminescence, fluorescence or phosphorescence using a known spectrophotometer and measurement reagents, and according to known measurement conditions (e.g., reaction time, measured wave length, etc.), and a procedure for performing an ELISA, etc., except for treating the atmosphere surrounding the reaction vessel and/or the atmosphere surrounding the reaction vessel in the photometry chamber, or blocking a contact of the atmosphere in the photometry chamber with the solution in the reaction vessel, and are not particularly limited. For details, the measurement may be performed by using each measuring instrument and reagents, according to a manual of each instruments and reagents.

A practical measurement method for generating an energy variation of a substance induced by the objective component in the sample, is not particularly limited, as long as it is a method for making the above-described substance which generates light present in the solution together with the sample containing the objective component to be measured, carrying out various types of reaction which generates energy variation in the presence of the substance, and measuring the amount of light such as luminescence, fluorescence or phosphorescence resulted from the reaction, and measuring the objective component in the sample using the measured value thus obtained.

This kind of reaction includes the known method, for example, the method for reacting the objective component with an oxidase of which the objective component is a substrate to produce hydrogen peroxide in a solution such as an appropriate buffer solution, and generating an appropriate energy variation by reacting this hydrogen peroxide with an appropriate chemical compound, and the method for reacting an labeled antibody specifically bind to the objective component which labeled with an oxidase such as POD with the objective component to produce an immune complex of the objective component and the labeled antibody, and then reacting the (POD labeled) immune complex with a substrate such as hydrogen peroxide and luminol, and measuring the generated energy variation (for example, luminescence, fluorescence or phosphorescence) by the reaction.

Besides, in the above-described method, the objective component may participate in main reaction either directly or secondarily (indirectly).

In order to avoid influences of substances other than the objective component contained in the sample, or to increase the detection sensitivity to the objective component, additives commonly used in this field such as a surfactant or an activator agent may be added.

Such measurement method includes those generally used, for example, a chemical measurement method (e.g. chelation luminescence method), an enzymatic measurement method (e.g. an oxidation-reduction luminescence method), and an immunological measurement method [e.g. an enzyme immunoassay (EIA), a fluoroimmunoassay (FIA), an immunological inhibition method, a chemiluminescence method, etc.] used in the field of, for example, clinical laboratory, biochemistry, biology, chemistry, food and environmental research. The measurement mechanism thereof may be a variety of procedures including a sandwich method, a competitive method and a double antibody technique, etc.

A chemiluminescent substance, a fluorescent substance or phosphorescent substance in order to measure luminescence, fluorescence or phosphorescence induced by the presence of the objective component to be measured in a measurement method for the present invention includes a substance usually used in the fields such as enzyme immunoassay (EIA), radioimmunoassay (RIA) and fluoroimmunoassay (FIA).

The chemiluminescent substance includes, for example, luminol derivatives such as isoluminol, luminol, aminoethylisoluminol, aminoethyl ethyl isoluminol, aminopropylisoluminol, aminobutylisoluminol, aminohexyl ethyl isoluminol, etc.; and luciferin, bis(2,4,6-trifluorophenyl)oxalate, etc.

The fluorescent substance includes, for example, a substance usually used in fluorescent immunoassay such as fluorescein, dansyl, fluorescamine, coumarin, naphthylamine, fluorescein isothiocyanate, rhodamine, rhodamine-X, sulforhodamine 101, lucifer yellow, acridine, acridine isothiocyanate, riboflavin or derivatives thereof and europium (Eu), etc.

The phosphorescent substance includes, for example, a mixture of sulfides of alkaline earth metals (e.g., calcium, and the like) and a small amount of heavy metals (e.g., cupper, and the like), methyl substituted benzoxazole, or benzophenone.

The measurement may be performed by generating luminescence by a luminescent substance, fluorescence by a fluorescent substance and phosphorescence by phosphorescent substance, corresponding to the amount of the objective component in the sample, and measuring the respective signal value.

For example, the method for measuring TSH (thyroid-stimulating hormone) in a sample by the method of the present invention is exemplified below.

A sample, polystyrene beads immobilized with an anti-TSH monoclonal antibody, POD-labeled anti-TSH monoclonal antibody solution, a 5 mM luminol solution and a $H_2O_2$ solution are each loaded on an automated analyzer which equipped with a mechanism for making the atmosphere surrounding the reaction vessel and/or the atmosphere surrounding the reaction vessel in the photometry chamber electrically constant of the present invention. After that, the analyzer is activated, the sample containing TSH and polystyrene beads immobilized with the anti-TSH monoclonal antibody are added and reacted, followed by B/F separation, POD-labeled anti-TSH monoclonal antibody is added thereto and reacted. Subsequently, the beads after B/F separation are added with a 5 mM luminol solution (a luminescent substrate) and a $H_2O_2$ solution, mixed, and then luminescence of the sample may be measured.

When a common spectrophotometer is used instead of the automated analyzer for measuring the above-described TSH, a sample and various reagents are reacted by manual means, luminescent reaction is occurred, after that, the reaction vessel is set in a spectrophotometer equipped with the mechanism for making an atmosphere surrounding the reaction vessel and/or the atmosphere surrounding the reaction vessel in the photometry chamber electrically constant of the present invention, and then, luminescence of the sample may be measured.

Additionally, another embodiment of the measuring method of the present invention includes, luminescence in a sample may be measured by using the spectrophotometer equipped with a mechanism for blocking the contact of the atmosphere in the photometry chamber with the solution in the reaction vessel. Typically, for example, the methods (i), (ii) or (iii) described below are included.

(i) A sample, polystyrene beads immobilized with an anti-TSH monoclonal antibody, peroxidase (POD)-labeled anti-TSH monoclonal antibody solution, a 5 mM luminol solution and a $H_2O_2$ solution are each loaded on an automated analyzer which equipped with a mechanism for shutting the opening part of the reaction vessel with the sheet of the present invention. After that, the analyzer is activated, the sample containing TSH and polystyrene beads immobilized with the anti-TSH monoclonal antibody are added and reacted, followed by B/F separation, peroxidase (POD)-labeled anti-TSH monoclonal antibody is added thereto and reacted. After that, the beads after B/F separation are added with a 5 mM luminol solution (a luminescent substrate) and a $H_2O_2$ solution, and mixed. Subsequently, the opening part of the reaction vessel is shut with the sheet by a mechanism equipped in the automated analyzer, and then luminescence of the sample may be measured.

When a common spectrophotometer is used instead of an automated analyzer for measuring the above-described TSH, a sample and various reagents are reacted by a manual means, luminescent reaction is occurred, after that, the opening part of the reaction vessel is shut by sealing, for example, with a cellophane tape, and then, the reaction vessel is set in a spectrophotometer, and then, luminescence of the sample may be measured.

(ii) A sample, polystyrene beads immobilized with an anti-TSH monoclonal antibody, peroxidase (POD)-labeled anti-TSH monoclonal antibody solution, a 5 mM luminol solution and a $H_2O_2$ solution are each loaded on an automated analyzer which equipped with a mechanism for dropping on (or run in) liquid which is insoluble in the solution in the vessel and has a property of spreading over the surface of the solution in the vessel. After that, the analyzer is activated, the sample containing TSH and polystyrene beads immobilized with an anti-TSH monoclonal antibody are added and reacted, followed by B/F separation, peroxidase (POD)-labeled anti-TSH monoclonal antibody is added thereto and reacted. After that, the beads after B/F separation are added with a 5 mM luminol solution (a luminescent substrate) and a $H_2O_2$ solution, and mixed. Subsequently, liquid which is insoluble in the solution in the vessel and has a property of spreading over the surface of the solution is dropped on (or run in) the surface of the solution in the reaction vessel to make a water-insoluble membrane by using a mechanism equipped in the automated analyzer, and then luminescence of the sample may be measured.

When a common spectrophotometer is used instead of an automated analyzer for measuring the above-described TSH, a sample and various reagents are reacted by a manual means, luminescent reaction is occurred, after that, liquid which is insoluble in the solution in the vessel and has a property of spreading over the surface of the solution in the reaction vessel is dropped or run in gently alongside the wall of a reaction vessel on the surface of the solution to make a water-insoluble membrane, and the reaction vessel is set in a spectrophotometer, and then, luminescence of the sample may be measured.

(iii) A sample, polystyrene beads immobilized with an anti-TSH monoclonal antibody, peroxidase (POD)-labeled anti-TSH monoclonal antibody solution, a 5 mM luminol solution and a $H_2O_2$ solution are each loaded on an automated analyzer, which equipped with a mechanism for applying (floating) a substance which has lower specific gravity than the solution in the reaction vessel, insoluble in the solution and has a property of floating on the surface of the solution on the surface of the solution. After that, the analyzer is activated, the sample containing TSH and polystyrene beads immobilized with the anti-TSH monoclonal antibody are added and reacted, followed by B/F separation, peroxidase (POD)-labeled anti-TSH monoclonal antibody is added thereto and reacted. After that, the beads after B/F separation are added with a 5 mM luminol solution (a luminescent substrate) and a $H_2O_2$ solution, and mixed. Subsequently, the substance which is insoluble in the solution in the vessel and has lower specific gravity than the solution and has a property of floating on the surface of the solution is applied (floated) to cover the surface of the solution in the vessel by using a mechanism equipped in the automated analyzer, and then luminescence of the sample is measured.

When a common spectrophotometer is used instead of an automated analyzer for measuring the above-described TSH, a sample and various reagents are reacted by a manual means, luminescence reaction is occurred, after that, the substance which is insoluble in the solution in the reaction vessel and has lower specific gravity than the solution in the vessel and has a property of floating on the surface of the solution is applied (floated) to cover the surface of the solution in the vessel, and the reaction vessel is set in a spectrophotometer, and then, luminescence of the sample is measured.

A method for obtaining an amount of the objective component in the sample on the basis of the measured values thus obtained may be determined in accordance with a protocol of each spectrophotometer used. For example, the signal value obtained by the above-mentioned method is applied to a calibration curve showing a relationship between concentration and a signal value which is previously obtained by measuring a standard solution containing a known amount of the objective component after a similar method as mentioned above whereby an amount of the objective component in the sample can be obtained. In addition, in the method described above, an amount of the objective component in the sample can be determined by subtracting a blind value, which is obtained by measuring a sample in which an objective component is not contained after a similar method as mentioned above from the measured signal value.

The objective components which can be measured by the method of the present invention are not particularly limited and any component can be measured as long as it has reactivity to produce luminescence, fluorescence, phosphorescence or absorption of light corresponding to the amount of the objective component to be measured [an objective component may participate in main reaction of the reaction either directly or secondarily (indirectly)], and which can be measured by spectrophotometry according to the generated light. Such component includes, for example, environmental hormone such as estrogen and bisphenol-A; tumor markers such as α-fetoprotein (AFP), CA19-9, a prostate-specific antigen (PSA) and a carcinoembryonic antigen (CEA); serum proteins such as immunoglobulin A (IgA), immunoglobulin E (IgE), immunoglobulin G (IgG), immunoglobulin M (IgM), $β_2$-microglobulin and albumin; enzymes such as amylase and alkaline phosphatase; in vivo substances such as cholesterol, triglyceride, creatinine and uric acid; drugs such as steroids, acetaminophens and digoxin compounds; non-peptide hormone such as estradiol and prolactins; DNA measuring reagents such as oligonucleotides complemental to nucleic acid components derived from various microorganisms, mycoplasmas and various viruses.

Examples of a sample are those containing the objective component to be measured as described above, and includes, for example, a sample derived from a living body which is exemplified by various body fluids such as serum, plasma, spinal fluid, saliva and pancreatic fluid, excrements such as urine and fecal matter (or its dilution), lymphocytes, blood cells, various cells, and tissue extracts of living body; a sample derived from plants such as plant tissue extracts or cell extracts; a sample derived from microorganisms such as culture medium and cell extracts; and a sample derived from food derivatives such as food staff or extracts thereof. These samples are usually used in the field of clinical laboratory, biochemistry, biology, chemistry of food science, etc.

The instrument of the present invention contains a mechanism for measuring value of light generated due to the energy variation of a substance and (a) a mechanism for making an atmosphere surrounding a reaction vessel and/or an atmosphere surrounding the reaction vessel in the photometry chamber electrically constant, or (b) a mechanism for blocking a contact of an atmosphere in the photometry chamber with the solution in a reaction vessel.

A typical examples of the mechanism in the above (a) for making an atmosphere surrounding a reaction vessel and/or an atmosphere surrounding the reaction vessel in the photometry chamber electrically constant includes one or more of mechanisms selected from the group consisting of; (1) an apparatus for flowing gas having a constant electric charge to surrounding the reaction vessel and/or into the photometry chamber, (2) an neutralization apparatus, or (3) a photometry chamber on which a material having a static electricity elimination effect is attached. Such mechanism is not limited to the above concrete examples as long as it can make the atmosphere surrounding the reaction vessel and/or the atmosphere surrounding the reaction vessel in the photometry chamber electrically constant according to the present invention. The typical examples of each constitutional element are as described above. That is, the instrument of the present invention can be obtained by equipping one or more of mechanism selected from examples described above, to a spectrophotometer used for the present invention.

A typical examples of mechanism (b) for blocking a contact of the atmosphere in the photometry chamber with the solution in the reaction vessel includes one or more of mechanism selected from the group consisting of; (1) an mechanism for shutting an opening part of a reaction vessel holding the solution with a sheet, (2) a mechanism for covering the surface of the solution with liquid which is insoluble in the solution and spreads over surface of the solution by dropping (or running in), (3) a mechanism for applying (floating) a substance which has lower specific gravity than the solution in the reaction vessel, insoluble in the solution and has a property of floating on the surface of the solution. Such mechanism is not limited to the above concrete examples as long as it can block a contact of the atmosphere in the photometry chamber with the solution in the reaction vessel according to the present invention. The typical examples of each constitutional element are as described above.

In addition, an instrument of the present invention may be equipped either with the above-described (a) the mechanism for making the atmosphere surrounding the reaction vessel and/or the atmosphere surrounding the reaction vessel in the photometry chamber electrically constant, or (b) the mechanism for blocking a contact of the atmosphere in the photometry chamber with the solution in the reaction vessel either independently or in combination of (a) and (b). Quite naturally, such mechanism may comprise both of plural mechanism (a) and plural mechanism (b) both in plural number.

Therefore, according to the present invention, the instrument of the present invention can be obtained only by equipping the above-described mechanism to the spectrophotometer which is conventionally used. This provides great advantage due to no need for measuring instrument equipped with a particular kind of mechanism for preventing the influence of the electric charge.

According to the present invention, between-day variation of signal value and background value can be reduced easily and simply only by making an atmosphere surrounding the reaction vessel and/or the atmosphere surrounding the reaction vessel in the photometry chamber electrically constant, or by blocking a contact of the atmosphere in the photometry chamber with the solution in the reaction vessel. In other words, a conventional problem was that accurate measurement could not be performed because of variation of signal value when a in vivo trace component is determined by measuring luminescence, fluorescence, phosphorescence and the like. After all, a problem lasted for a long time without favorable improvement, even though various intensive studies have been carried out to overcome such trouble. These problems can be solved easily and quite unexpectedly by the present invention.

Effects Of The Invention

According to the present invention, in measurement of an objective component to be measured in a sample by spectrophotometric measurement of light generated due to an energy variation using a spectrophotometer, problems such as between-day variation of signal value or increase of background value can be solved, and a trace component can be measured in high accuracy and high sensitivity.

The present invention will be explained further in detail by referring to Examples, but the present invention is not construed as limiting to these Examples.

EXAMPLES

Experimental Example 1

Investigation of a Variation of Measured Value Caused by Environmental Changes

[Preparation of Reagents]

Following reagents were prepared:

Distilled water,

Reagent A: a solution of 5 mM luminol (a buffer solution exclusive for SphereLight 180, pH 8.5, Wako Pure Chemical Industries, Ltd.), Reagent B: an aqueous solution of 0.02% $H_2O_2$, Reagent C: a mixture of equal volume of Reagent A and Reagent B.

[Measurement of Luminescence]

Luminescence of 140 μL of each reagent prepared in above was measured by using SphereLight 180 which was automated chemiluminescence enzyme immunoassay analyzer (SphereLight 180, Olympus Ltd.) as a measuring instrument. Measurement was repeated 10 times (every 20 seconds in this Example) at the same interval in the same sample.

Also, the measurement was carried out 10 times at different days by the same method as described above, and the variation of measured value (signal value) for every measurement and the between-day variation were investigated.

[Results]

Results are shown in Table 1-1 and Table 1-2. Table 1-1 shows the results of the first measurement day, and Table 1-2 shows results of the second measurement day (Unit: cps).

TABLE 1-1

| Number of Measurement | Water | Reagent A | Reagent B | Reagent C |
|---|---|---|---|---|
| 1 | 19 | 19 | 11 | 1,199 |
| 2 | 11 | 21 | 10 | 1,118 |
| 3 | 21 | 19 | 21 | 1,174 |
| 4 | 16 | 24 | 20 | 1,167 |
| 5 | 9 | 29 | 19 | 1,118 |
| 6 | 20 | 25 | 17 | 1,144 |
| 7 | 9 | 28 | 10 | 1,134 |
| 8 | 14 | 37 | 14 | 1,174 |
| 9 | 18 | 21 | 12 | 1,168 |
| 10 | 10 | 26 | 15 | 1,188 |
| Average | 14.7 | 24.9 | 14.9 | 1,158.4 |

TABLE 1-2

| Number of Measurement | Water | Reagent A | Reagent B | Reagent C |
|---|---|---|---|---|
| 1 | 16 | 86 | 18 | 2,452 |
| 2 | 9 | 107 | 12 | 2,126 |
| 3 | 22 | 78 | 11 | 2,531 |
| 4 | 13 | 80 | 17 | 2,262 |
| 5 | 12 | 76 | 16 | 2,221 |
| 6 | 11 | 79 | 20 | 2,943 |
| 7 | 18 | 90 | 13 | 2,174 |
| 8 | 12 | 86 | 17 | 3,035 |
| 9 | 17 | 87 | 15 | 2,173 |
| 10 | 20 | 79 | 11 | 2,091 |
| Average | 15.0 | 84.8 | 15.0 | 2,400.8 |
| Difference Compared with Table 1-1 (cps) | 0.3 | 59.9 | 0.1 | 1,242.4 |

As is clear from Table 1-1 and Table 1-2, any variation of signal value is not observed in water and reagent B containing $H_2O_2$ even when luminescence is measured at different day (water: 0.3 cps, $H_2O_2$: 0.1 Cps). On the contrary, reagent A and reagent C both containing luminol shows extreme between-day variation (between-day variation of reagent A: 59.5 cps, between-day variation of reagent C: 1,242.4 cps).

Any variation of signal value is not observed in the measurement using water as a sample. Therefore, it is suggested that a noise and incorrect electric current running in a current-voltage converter are not a variation factor caused by environmental change at measured time. Also, the variation of the signal value is observed only in the reagent containing luminol. Therefore, it is suggested that energy condition of luminol is changed by environmental change at measured time, and then variation of background value is induced.

Example 1

Removal Effect of Electricity Using Anti-Static Tape
[Preparation of Reagents]
Following reagents were prepared:
A Luminescent substrate Solution: a solution of 5 mM luminol (a buffer solution exclusive for SphereLight 180, pH 8.5, Wako Pure Chemical Industries, Ltd.),
A $H_2O_2$ Solution: an aqueous solution of 0.02% $H_2O_2$ (an acid buffer solution exclusive for SphereLight 180, pH 3.0, Wako Pure Chemical Industries, Ltd.).

[Measuring Instrument]
SphereLight 180 which was automated chemiluminescence enzyme immunoassay analyzer (Olympus Ltd.) was used. One instrument attached the anti-static tape (25 mm wide, Japan Vilene Co., Ltd.) transversely on four inside wall surfaces of the photometry chamber, and the other instrument without attachment of anti-static tape were prepared.

[Measurement of Luminescence]
The luminescent substrate solution of 70 μL and 70 μL of a $H_2O_2$ solution prepared as above were automatically dispensed into the reactor tank of the reagent cartridge in SphereLight 180, and then, the luminescence of 140 μL in total volume of the reaction solution was measured. Incidentally, there is a concave portion to dispense the reagent solution in the above-described reagent cartridge, and it is called as a reactor tank (or called as a measurement vesell).

Measurement was repeated 4 times (every 20 seconds in this Example) at the same interval in the same sample.

[Results]
Results are shown in Table 2 (Unit: cps). In Table 2, "Control" means a result obtained by measuring luminescence using the measuring instrument on which an anti-static tape is not attached (Counter measure for preventing the influence of the electric charge is not provided.). The "versus Control" (%) is shown as a ratio of the average of signal values obtained by measuring luminescence using measuring instrument on which the anti-static tape is attached, to the average of the signal value of control.

TABLE 2

| Number of Measuremnet | Control | with Anti-static Tape | versus Control |
|---|---|---|---|
| 1 | 5,726 | 3,125 | |
| 2 | 5,491 | 3,356 | |
| 3 | 5,275 | 3,289 | |
| 4 | 5,599 | 3,054 | |
| Average | 5,523 | 3,206 | 58% |

As is clear from Table 2, the signal values measured by using the measuring instrument attached the anti-static tape thereon is 58% against control. Therefore, it is understood that the measurement using anti-static tape can suppress background value.

Example 2

Investigation of Attaching Position of an Anti-Static Tape
[Preparation of reagents] The same reagents as in Example 1 were used.

[Measuring Instrument]
In SphereLight 180 which was automated chemiluminescence enzyme immunoassay analyzer (Olympus Ltd.), two cases of the apparatus were set, that is the one with an anti-static tape (25 mm wide, Japan Vilene Co., Ltd.) attached on various positions of the inside wall surface of the photometry chamber (Patterns 2 to 8 in Table 3) and the other one without attachment of anti-static tape (Pattern 1 in Table 3).

Also, the attached position of the anti-static tape in the photometry chamber in patterns 1 to 8 was indicated by boldface in the Table 3 showing the photometry chamber and the set position of the reagent cartridge in the photometry chamber (Patterns 3 to 5 were set up so that the total size of attached anti-static tape were the same.).

That is, patterns 1 to 8 each show positions of the anti-static tapes were attached as follows:
Pattern 1: The case which the anti-static tape was not attached (Countermeasure for preventing the influence of the electric charge was not provided. Control).
Pattern 2: The case which anti-static tapes were attached on four inside wall surfaces (face A to face D) of the photometry chamber.
Pattern 3: The case which the anti-static tapes were attached on face A and face B of the photometry chamber.
Pattern 4: The case which the anti-static tapes were attached on face C and face D of the photometry chamber.
Pattern 5: The case which the anti-static tape was attached on only face A of the photometry chamber.
Pattern 6: The case which the anti-static tape was attached on only face B of the photometry chamber.
Pattern 7: The case the anti-static tapes were attached on longitudinal both sides of the reagent cartridge parallel to face A and face B of the photometry chamber.
Pattern 8: The case which the anti-static tapes were attached on longitudinal both sides of the reagent cartridge parallel to face A and face B of the photometry chamber, and also, on face A and face B of the photometry chamber.

Furthermore, a view showing a frame format of the photometry chamber in case of pattern 5 is shown in FIG. 1. In FIG. 1, four inside wall surfaces of the photometry chamber were shown as A, B, C and D each, and these symbols correspond to A, B, C and D in the Figure showing the attached position for attachment of an anti-static tapes in photometry chamber in pattern 1 of Table 3, respectively. Also, the attached position of the anti-static tape, the position of the photometry chamber, the position of the photoelectron multiplier against to the photometry chamber, and setting position of the reagent cartridge holding the reaction solution are shown in FIG. 1. That is, the anti-static tape was attached in the photometry chamber, and the photoelectron multiplier is located on wall side of face A of a photometry chamber.

[Measurement of Luminescence]

The luminescent substrate solution of 70 μL and 70 μL of the $H_2O_2$ solution prepared as above were automatically dispensed into the reactor tank of the reagent cartridge in SphereLight 180, and then, luminescence of 140 μL in total volume of reaction solution was measured. Measurement was repeated 5 times (every 20 seconds in this Example) at the same interval in the same reaction solution.

[Results]

Results are shown in Table 3 (Unit: cps). In Table 3, A, B, C and D shown in Figure of attached position of anti-static tape in photometry chamber in pattern 1 corresponds to A, B, C and D in FIG. 1, respectively.

Also, the result (Pattern 1) obtained by measuring luminescence using the measuring instrument on which an anti-static tape is not attached is determined as control. Also, "versus Control" (%) is shown as a ratio of the average of the signal values obtained by measuring luminescence using measuring instrument of each pattern, to the average of the signal value of control.

Example 3

Influence of Electrification of a Reagent Cartridge and Grounding Effect on the Measurement

[Preparation of Reagents] The same reagents as in Example 1 were used.

[Measuring Instrument]

In SphereLight 180 which was automated chemiluminescence enzyme immunoassay analyzer (Olympus Ltd.), aluminum foil was set at the undersurface of the photometry chamber (set position of aluminum foil was shown by oblique lines in FIG. 2), and also, an anti-static tape (25 mm wide, Japan Vilene Co., Ltd.) was attached on four inside wall surfaces of the photometry chamber.

In addition, when the reagent cartridge is set (FIG. 1), the reagent cartridge contacts with aluminum foil which was set at the undersurface of the photometry chamber. And the aluminum foil contacts with the screw at the undersurface of the photometry chamber, and the screw is connected to the grounding of the instrument body. Therefore, when the reagent cartridge becomes electrically charged, the electric charge is removed through the aluminum foil.

Other instruments which were equipped mechanisms described in table. 4, for example, the instruments without aluminum foil were also prepared.

[Measurement of Luminescence]

The luminescent substrate solution of 70 μL and the 70 μL of $H_2O_2$ solution prepared as above were automatically dispensed into the reactor tank of the reagent cartridge in SphereLight 180, and then, luminescence of 140 μL in total volume of the reaction solution was measured. Measurement was

TABLE 3

| Pattern | 1 | 2 | 3 | 4 | 5 | 6 | 7 | 8 |
|---|---|---|---|---|---|---|---|---|
| Attached Position of Anti-static Tape in Photometry Chamber | (C top, A left, B right, D bottom) | | | | | | | |
| Number of Measurement 1 | 4,199 | 2,222 | 1,979 | 2,042 | 2,974 | 2,716 | 2,447 | 1,837 |
| 2 | 4,451 | 2,267 | 2,069 | 1,833 | 3,163 | 3,711 | 1,664 | 2,028 |
| 3 | 5,806 | 2,630 | 1,680 | 2,528 | 2,909 | 3,158 | 2,238 | 1,705 |
| 4 | 4,327 | 1,888 | 2,114 | 2,446 | 3,601 | 2,984 | 3,002 | 1,546 |
| 5 | 5,202 | 2,147 | 1,532 | 2,383 | 2,999 | 2,960 | 1,611 | 2,028 |
| Average | 4,797 | 2,231 | 1,875 | 2,246 | 3,129 | 3,106 | 2,192 | 1,829 |
| versus Control | 100% | 47% | 39% | 47% | 65% | 65% | 46% | 38% |

The position of an anti-static tape is attached

As is clear from Table 3, it is understood that background value can be suppressed when luminescence is measured by using the instrument attached the anti-static tapes thereon.

In particular, in patterns 2, 3, 4, 7 and 8 of Table 3, background value is found to be suppressed to not higher than 50% (value of "versus Control" is low). From the results, it is found that to attach the anti-static tape on the position where the reagent cartridge is sandwiched between both sides is especially effective.

repeated 5 times (every 20 seconds in this Example) at the same interval in the same reaction solution.

[Results]

Results are shown Table 4 (Unit: cps). In Table 4, the result obtained by measuring luminescence using the measuring instrument in which countermeasure for preventing the influence of the electric charge is not provided is determined as control. Also, "versus Control" (%) is shown as a ratio of the average of signal values obtained by measuring luminescence using measuring instrument in which countermeasure for preventing the influence of the electric charge is provided, to the average of the signal value of control.

TABLE 4

| Aluminum Foil at the undersurface of photometry chamber | without | without | with |
|---|---|---|---|
| Anti-static Tape on photometric chamber | without | with | without |
| Number of Measurement | | | |
| 1 | 6,733 | 3,192 | 8,408 |
| 2 | 6,608 | 3,282 | 7,591 |
| 3 | 6,321 | 3,230 | 7,681 |
| 4 | 6,980 | 2,740 | 7,342 |
| 5 | 7,105 | 3,744 | 7,754 |
| Average | 6,749 | 3,238 | 7,755 |
| versus Control | 100% | 48% | 115% |

As is clear from Table 4, background value can not be suppressed even though the electric charge of the reagent cartridge is removed by setting the aluminum foil at the undersurface of the photometry chamber (The value of versus Control is high.). From this result, it becomes clear that electrostatic charge of the reagent cartridge does not affect on the increase of background value. That is, it is understood from the result that background value cannot be suppressed even though the grounding is set in the photometry chamber. The other hand, background value can be suppressed by attaching an anti-static tape in the photometry chamber even without grounding.

Example 4

Effect of Exchanging an Atmosphere Surrounding a Reactor Tank in a Photometry chamber with Gas Having a Constant Electric Charge

[Preparation of Reagents] The same reagents as in Example 1 were used.

[Measuring Instrument] Using SphereLight 180 which was automated chemiluminescence enzyme immunoassay analyzers (Olympus Ltd.), an air blowing tube was installed in its photometry chamber so that atmospheric air was blown into the photometry chamber by a pump (xx5510000, Millipore Co., Ltd).

[Measurement of Luminescence]

Measurement of luminescence was conducted by the same method as in Example 1, except that countermeasure for preventing the influence of the electric charge was performed by using the above-described measuring instrument. That is, the external air was continuously blown during measurement into the photometry chamber by the pump, and the electric charge of the atmosphere surrounding the reaction vessel in the photometry chamber was maintained constant.

Measurement was repeated 4 times at the same interval (every 20 seconds in this Example) in the same reaction liquid.

[Results]

R: cps). In Table 5, control means a result obtained by measuring luminescence under the condition without blowing air (Countermeasure for preventing the influence of the electric charge is not provided.).

Also, "versus Control" (%) is shown as a ratio of the average of the signal values obtained by measuring luminescence under air exchange, to the average of signal value of control.

TABLE 5

| Number of Measurement | Control | Air Exchange | versus Control |
|---|---|---|---|
| 1 | 4,940 | 3,317 | |
| 2 | 5,184 | 3,556 | |
| 3 | 5,189 | 3,506 | |
| 4 | 5,230 | 3,295 | |
| Average | 5,136 | 3,419 | 67% |

As is clear from Table 5, the signal value (versus control value) is 67% when the atmosphere surrounding the reaction vessel in the photometry chamber is exchanged with the external air. Therefore, it is understood that background value can be suppressed by exchanging the atmosphere surrounding the reaction vessel in the photometry chamber with the external air.

Example 5

Effect of Utilization of Neutralization Apparatus

[Preparation of Reagents] The same reagents as in Example 1 were used.

[Measuring Instrument] Using SphereLight 180 which was automated chemiluminescence enzyme immunoassay analyzers (Olympus Ltd.), a neutralization apparatus (SJ01 SJ020, Keyence Co., Ltd.) was installed at the position so that electric charge surrounding the reaction vessel of the reagent cartridge could be neutralized just before measuring operation. And charge neutralization around the reagent cartridge was carried out by using the apparatus.

[Measurement of Luminescence]

Luminescence was measured by the same method as Example 1, except that the measuring instrument with charge neutralization countermeasure was used.

Measurement was repeated 4 times (every 20 seconds in this Example) at the same interval in the same reaction solution.

[Results]

Results are shown in Table 6 (Unit: cps). In Table 6, "Control" means a result obtained by measuring luminescence by using measuring instrument without a neutralization apparatus (Countermeasure for preventing the influence of the electric charge is not provided.). Also, "versus Control" (%) is shown as a ratio of the average of signal values obtained by the measuring luminescence using the measuring instrument with neutralization apparatus is installed therein, to the average of the signal value of control.

TABLE 6

| Number of Measurement | Control | with Neutralization Apparatus | versus Control |
|---|---|---|---|
| 1 | 6,084 | 2,942 | |
| 2 | 6,946 | 3,687 | |
| 3 | 6,948 | 3,279 | |
| 4 | 6,885 | 3,837 | |
| Average | 6,716 | 3,436 | 51% |

As obvious from Table 6, the signal value is 51% when the charge neutralization treatment is carried out for the reagent cartridge using the neutralization apparatus. This means that background value is suppressed by charge neutralization treatment of the present invention.

Example 6

Measurement of an Analyte with the Prevention of the Influence of the Electric Charge

[Preparation of Samples and Reagents]

As samples, 0, 0.01, 0.1, 2.5, 10 and 100 μIU/ml of TSH (Thyroid Stimulating Hormone) (Solvent: Diluting Solution of Analyte, Wako Pure Chemical Industries, Ltd.) were prepared.

As reagents, SphereLight TSH III-measuring reagent kit (Wako Pure Chemical Industries, Ltd.) with the following constitution was prepared.

Solid Phase: Polystyrene beads (⅛ inches) immobilized with an anti-TSH monoclonal antibody, A Labeled Antibody Solution: A peroxidase (POD)-labeled anti-TSH monoclonal antibody, A Diluting Solution of Analyte: A diluting solution of analyte exclusive for SphereLight 180, A Luminescent Substrate Solution: A solution of 5 mM luminol (a buffer solution exclusive for SphereLight 180, pH 8.5, Wako Pure Chemical Industries, Ltd.), A $H_2O_2$ Solution: An aqueous solution of 0.02% $H_2O_2$, (an acid buffer solution exclusive for SphereLight 180, pH 3.0, Wako Pure Chemical Industries, Ltd.).

[Measuring Instrument]

Using SphereLight 180 which was automated chemiluminescence's enzyme immunoassay analyzers (Olympus Ltd.), following instrument was used under condition as described below.

(1) The instrument in which countermeasure for preventing the influence of the electric was not provided, (2) The instrument which the anti-static tapes attached transversely on four inside wall surfaces of the photometry chamber, in the same way as Example 1 (A preventing method a), (3) The instrument which the anti-static tapes attached transversely on four inside wall surfaces of the photometry chamber, and moreover, a neutralization apparatus (SJ01 SJ020, Keyence Co., Ltd.) installed at the position so that electric charge surrounding the reaction vessel of the reagent cartridge could be neutralized, in order to electric charge surrounding the reagent cartridge was neutralized (A preventing method b).

[Measurement of Luminescence]

The TSH sample of 50 μL with each concentration prepared by the above method and 90 μL of the diluting solution of analyte were added into the reaction vessel holding the above beads immobilized with the anti-TSH antibody, mixed, and reacted at 37° C. for 7 minutes. After the reaction, the beads were washed, and 140 μL of the POD-labeled anti-TSH antibody solution was added thereto, and mixed, followed by allowing a reaction to take place at 37° C. for 7 minutes. After the reaction, the beads were washed, and the luminescent substrate solution of 70 μL and 70 μL of the $H_2O_2$ solution were added thereto and mixed. After mixing, luminescence in the reaction solution was measured.

[Results]

Results are shown in Table 7 (Unit: cps)

In Table 7, "S/N" means the radio of "a value obtained by measuring the luminescence of the sample containing each concentration of TSH" to "a value obtained by measuring the luminescence of the sample which does not contain TSH by the same method as described above.

TABLE 7

| Sample | without Preventing Method | | | Preventing Method a | | | Preventing Method b | | |
|---|---|---|---|---|---|---|---|---|---|
| (μIU/mL) | Data | Average | S/N | Data | Average | S/N | Data | Average | S/N |
| 0 | 17,745 | | | 6,434 | | | 5,479 | | |
| | 17,991 | 17,868 | 1.00 | 6,413 | 6,424 | 1.00 | 5,580 | 5,530 | 1.00 |
| 0.01 | 19,589 | | | 9,185 | | | 8,535 | | |
| | 19,607 | 19,598 | 1.10 | 9,051 | 9,118 | 1.42 | 8,563 | 8,549 | 1.55 |
| 0.1 | 54,249 | | | 44,794 | | | 43,022 | | |
| | 51,188 | 52,719 | 2.95 | 43,292 | 44,043 | 6.86 | 43,822 | 43,422 | 7.85 |
| 2.5 | 1,341,577 | | | 1,404,537 | | | 1,384,086 | | |
| | 1,398,990 | 1,370,284 | 76.69 | 1,314,811 | 1,359,674 | 211.67 | 1,320,636 | 1,352,361 | 244.57 |
| 10 | 5,569,448 | | | 5,387,652 | | | 5,594,896 | | |
| | 5,286,842 | 5,428,145 | 303.79 | 5,235,523 | 5,311,588 | 826.90 | 5,291,060 | 5,442,978 | 984.35 |
| 100 | 31,232,604 | | | 29,786,674 | | | 29,248,316 | | |
| | 33,460,552 | 32,346,578 | 1,810.31 | 31,718,816 | 30,752,745 | 4,787.54 | 31,863,476 | 30,555,896 | 5,525.98 |

As is clear from Table 7, sensitivity improvement (improvement of S/N ratio) is recognized in luminescence measurement by carrying out the method for preventing the influence of the electric charge of the present invention. Also, when two methods for preventing are combined (a preventing method b), better effect of sensitivity improvement (improvement of S/N ratio) is obtained. Therefore, it is suggested that the effect of sensitivity improvement is further enhanced with combination of appropriate method for preventing the influence of the electric charge in the present invention.

Example 7

Suppression of Signal Value Variation Caused by Environmental Change

Using the same reagents as in Example 1, measurements were carried out for different three days (Environment A, Environment B and Environment C). Measurement was repeated 4 times (every 20 seconds in this Example) at the same interval in the same reaction solution.

Measurements were carried out by using the instrument attached the anti-static tapes transversely on four inside wall surfaces of the photometry chamber, similarly as in Example 1. The measurement using the instrument without attachment of the anti-static tapes (Countermeasure for preventing the influence of the electric charge was not provided.) was carried out, and the obtained result was determined as control.

Results are shown in Table 8-1 and Table 8-2, and the former shows a result of control, and the latter shows result obtained by the measurement using the instrument which the anti-static tape attached thereon, respectively. In Table 8-1 and Table 8-2, the average of four times measured values obtained at the first measurement day (Environment A) was determined as 100, and "/Environment A" means a relative percentage (%) of measured value in each environment (A to C) to the determined values which described above.

TABLE 8-1

| Number of Measurement | Environment A | Environment B | Environment C |
|---|---|---|---|
| 1 | 4,069 | 15,155 | 20,745 |
| 2 | 3,943 | 14,379 | 20,991 |
| 3 | 3,935 | 14,681 | 21,450 |
| 4 | 4,291 | 14,934 | 22,948 |
| Average | 4,060 | 14,787 | 21,534 |
| / Environment A | 100% | 364% | 530% |

TABLE 8-2

| Number of Measurement | Environment A | Environment B | Environment C |
|---|---|---|---|
| 1 | 4,492 | 5,808 | 6,749 |
| 2 | 3,492 | 5,014 | 3,479 |
| 3 | 3,700 | 5,501 | 5,843 |
| 4 | 3,820 | 5,258 | 5,580 |
| Average | 3,876 | 5,395 | 6,163 |
| / Environment A | 100% | 139% | 159% |

As is clear from the result shown in Table 8-1 and Table 8-2, when the measurement is carried out by using the instrument in which the countermeasure for preventing the influence of the electric charge is not provided, obtained measurement value is varied significantly depending the measurement date (Environmental variation) (Table 8-1). Contrary to that, when the measurement is carried out by using the instrument which the anti-static tape is attached thereon, the obtained measurement value are not varied so much even though the measurement day is different, in other word, even in environmental variation (Table 8-1), and this means that stable measurement is achieved by the present invention.

Example 8

Improvement of Reproducibility of Measured Value by Charge Removal Countermeasure Using the same measuring kit as in Example 6, luminescence measurement in samples including 0.02 and 0.1 μIU/mL of TSH was carried out. Measurement was repeated 10 times (every 20 seconds in this Example) at the same interval in the same reaction solution.

The measurement was carried out by using an instrument attached the anti-static tapes transversely on four inside wall surfaces of a photometry chamber (with charge removal countermeasure), similarly as in Example 1, and an instrument without attachment of the anti-static tape (without charge removal countermeasure).

Results are shown in Table 9.

TABLE 9

| | without Charge Removal Countermeasure | | with Charge Removal Countermeasure | |
|---|---|---|---|---|
| | TSH 0.02 μIU/mL | TSH 0.1 μIU/mL | TSH 0.02 μIU/mL | TSH 0.1 μIU/mL |
| 1 | 24,455 | 53,054 | 13,961 | 42,452 |
| 2 | 20,696 | 52,343 | 13,336 | 43,237 |
| 3 | 21,923 | 50,918 | 13,425 | 41,334 |

TABLE 9-continued

| | without Charge Removal Countermeasure | | with Charge Removal Countermeasure | |
|---|---|---|---|---|
| | TSH 0.02 μIU/mL | TSH 0.1 μIU/mL | TSH 0.02 μIU/mL | TSH 0.1 μIU/mL |
| 4 | 22,856 | 48,184 | 13,865 | 42,534 |
| 5 | 22,235 | 55,788 | 12,672 | 42,755 |
| 6 | 18,807 | 49,932 | 13,209 | 40,838 |
| 7 | 20,656 | 52,404 | 13,084 | 40,881 |
| 8 | 20,415 | 50,944 | 12,949 | 41,640 |
| 9 | 18,677 | 48,801 | 13,666 | 40,581 |
| 10 | 17,709 | 51,214 | 13,868 | 42,243 |
| Average Value | 20,843 | 51,358 | 13,404 | 42,880 |
| SD Value | 2,084 | 2,201 | 434 | 946 |
| CV Value | 10.0% | 4.3% | 3.2% | 2.3% |

As is clear from Table 9, the measured value obtained by using the instrument with charge removal countermeasure shows less variation of measured value, and therefore, reproducibility of measured value is improved.

Example 9

Investigation on a Method for Shutting an Opening Part of a Reaction Vessel Holding a Solution

[Preparation of Reagents] The same reagents as in Example 1 were used.

[Measuring Instrument]

SphereLight 180 which was automated chemiluminescence enzyme immunoassay analyzer (Olympus Ltd.) was used similarly as in Example 1. To the instrument, countermeasure for preventing the influence of the electric charge was not provided.

[Measurement of Luminescence]

Measurement of luminescence was carried out under the following condition. Measurement was repeated 5 times (every 20 seconds in this Example) at the same interval in the same reaction solution. Incidentally, the reagent cartridge used for the measurement has a concave portion to dispense the reagent solution, and it is called as a reactor tank (or called as a measurement cell).

(1) The above-prepared reagents were dispensed and mixed into the reactor tank of the reagent cartridge (Total volume of reaction solution was 140 μL), and then, it was set in SphereLight 180 and luminescence was measured.

(2) After measurement of (1), the reagent cartridge was collected, and the opening part of the reactor tank was sealed with a cellophane tape (shut). And then, it was set in SphereLight 180 again, and luminescence was measured.

(3) After measurement of (2), the reagent cartridge was collected, and the cellophane tape was peeled off, it was set in SphereLight 180 again, and luminescence was measured.

(4) After measurement of (3), the reagent cartridge was collected, and the opening part of the reactor tank of the reagent cartridge was sealed with a cellophane tape (shut). And then, it was set in SphereLight 180 again, and luminescence was measured.

[Results]

Results are shown in Table 10 (Unit: cps). In Table 10, the result obtained by measuring luminescence under condition without sealing the reactor tank is determined as control. And "versus Control" (%) is shown as a ratio of the average of signal values obtained by each measurement method, to the average of the signal value of control.

TABLE 10

|  | Measuring Method | | | |
|---|---|---|---|---|
|  | (1) | (2) | (3) | (4) |
| Sealing of Reaction Tank | — | Sealed | — | Sealed |
| Number of Measurement | | | | |
| 1 | 1909 | 466 | 1981 | 524 |
| 2 | 2008 | 449 | 2285 | 469 |
| 3 | 1983 | 462 | 2113 | 513 |
| 4 | 2351 | 415 | 2135 | 513 |
| 5 | 2280 | 407 | 2211 | 523 |
| Average | 2106 | 440 | 2145 | 508 |
| versus Control | 100% | 21% | 102% | 24% |

As is clear from Table 10, background value is suppressed by sealing the opening part of the reactor tank with the cellophane tape whereby blocking the contact of the atmosphere in the photometry chamber with the solution in the reaction vessel (2).

After background value is confirmed to be suppressed, the cellophane tape is peeled off and again measurement is carried out, and the background value is increased again (3). However when luminescence is measured after sealing the opening part of the reactor tank again with the cellophane tape, the background value is suppressed again (4). From these results, it is suggested that background value varies by contacting atmosphere in the photometry chamber with the reagent.

Example 10

Investigation on Sheet to Shut the Opening Part of a Reaction Vessel

[Preparation of Reagents] The same reagents as in Example 1 were used.

[Measuring Instrument]

SphereLight 180 which was automated chemiluminescence enzyme immunoassay analyzers (Olympus Ltd.) was used. To the instrument, countermeasure for preventing the influence of the electric charge was not provided.

[Measurement of Luminescence]

The reagents prepared above were dispensed and mixed into the reactor tank of the reagent cartridge (total volume of reaction solution was 140 µL) and the opening part of the reactor tank was sealed (shut) with an aluminum seal or a cellophane tape, and then, it was set in SphereLight 180, and luminescence was measured. Measurement without sealing the opening part of the reactor tank was carried out, and obtained result determined as control. Measurement was repeated 5 times (every 20 seconds in this Example) at the same interval in the same reaction solution.

[Results]

Results are shown in Table 11 (Unit: cps). In Table 11, "versus Control" (%) is shown as a ratio of the average of the signal values obtained by measuring luminescence using the reagent cartridge with the opening part of the reactor tank sealed, to the average of signal values of control.

TABLE 11

| Seal of Reactor Tank | | without | covered | covered |
|---|---|---|---|---|
| Seal Type | | without | Aluminum Seal | Cellophane Tape |
| Number of | 1 | 1,697 | 604 | 459 |
| Measurement | 2 | 1,167 | 437 | 451 |
| | 3 | 1,425 | 618 | 408 |
| | 4 | 1,315 | 572 | 449 |
| | 5 | 1,039 | 589 | 489 |
| Average | | 1,329 | 564 | 451 |
| versus Control | | 100% | 42% | 34% |

As is clear from Table 11, background value can be suppressed by sealing (shutting) the opening part of the reactor tank with blocking the contact of the atmosphere surrounding the photometry chamber with the solution in the reaction vessel.

Also, background value can be suppressed at nearly the same level irrespective of whether shutting is carried out with the aluminum seal or the scotch seal.

Example 11

Investigation on a Method for Covering the Surface of a Reaction Solution with a Water-Insoluble Liquid

[Preparation of Reagents] The same reagents as in Example 1 were used.

[Measurement of Luminescence]

The above-prepared reagents were dispensed and mixed into the reactor tank of the reagent cartridge (Total volume of reaction solution was 140 µL), and then silicon oil (Shin-Etsu Silicon Co., Ltd) was funneled gently along the inside wall surface of the reactor tank using a pipette to the surface of the mixed reaction solution. And the surface of the reaction solution was covered with silicon oil to provide oil film.

And then, the reagent cartridge was set in SphereLight 180 and luminescence was measured. Similar measurement without covering the surface of the reaction solution was carried out, the obtained result was determined as control. Measurement was repeated 5 times (every 20 seconds in this Example) at the same interval in the same reaction solution.

[Measuring Instrument]

SphereLight 180 which was automated chemiluminescence enzyme immunoassay analyzer (Olympus Ltd.) was used. One instrument attached the anti-static tapes (25 mm wide, Japan Vilene Co., Ltd.) transversely on four inside wall surfaces of a photometry chamber, and the other instrument without attachment of the anti-static tape was prepared.

[Results]

Results are shown in Table 12 (Unit: cps). In Table 12, "versus Control" (%) is shown as a ratio of the average of the signal values obtained by measuring luminescence in the solution which treated its surface of reaction solution with silicone oil film, to average of signal values of control.

TABLE 12

| Anti-static Tape on Photometry Chamber | | without | without | with | with |
|---|---|---|---|---|---|
| Silicon Oil Film | | without | with | without | with |
| Number of | 1 | 1,765 | 802 | 1,615 | 673 |
| Measurement | 2 | 2,691 | 855 | 1,791 | 751 |
| | 3 | 2,097 | 864 | 1,467 | 783 |
| | 4 | 2,883 | 987 | 1,600 | 929 |
| | 5 | 3,733 | 1,037 | 2,175 | 824 |
| Average | | 2,634 | 909 | 1,730 | 792 |
| versus Control | | 100% | 35% | 66% | 30% |

As is clear from Table 12, background value can be suppressed by covering the surface of the reactor tank with silicon oil and by blocking the contact of an atmosphere surrounding the photometry chamber with the solution in the reaction vessel.

BRIEF DESCRIPTION OF THE DRAWINGS

In FIG. 1, four inside wall surfaces of the photometry chamber are shown as A, B, C and D, respectively. Also, the attached position of the anti-static tape, the position of the photometry chamber, the position of the photoelectron multiplier against the photometry chamber, and setting position of the reagent cartridge holding reaction solution are shown.

In FIG. 2, four inside wall surfaces of the photometry chamber are shown as A, B, C and D, respectively. Also, the set position of aluminum foil in the photometry chamber is shown by oblique lines.

Figure 1:
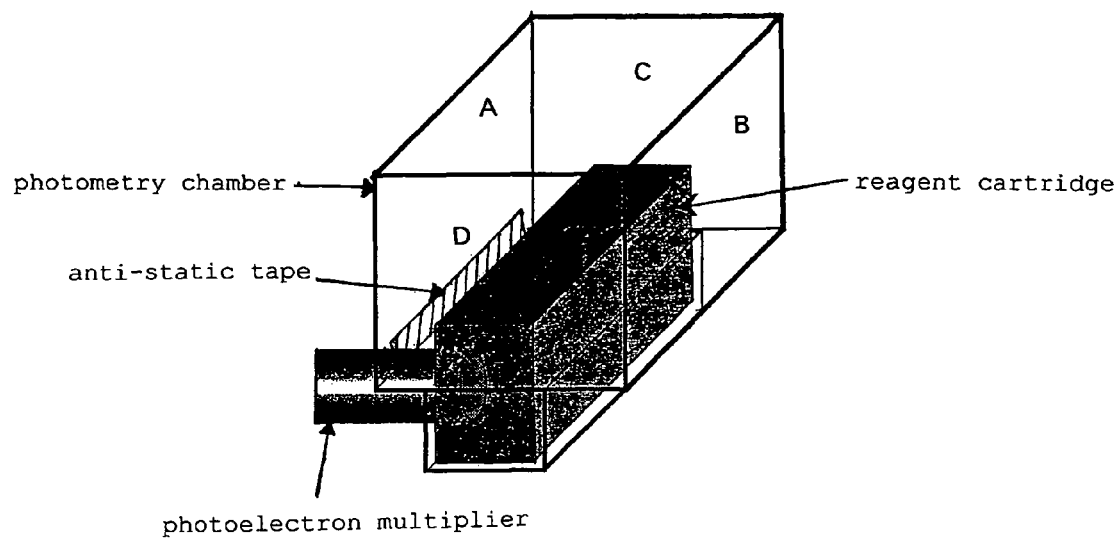
[FIG. 1] A view showing a frame format of the photometry chamber of SphereLight 180 which is automated chemiluminescence enzyme immunoassay analyzer used in pattern 5 of Example 2.
Figure 2:
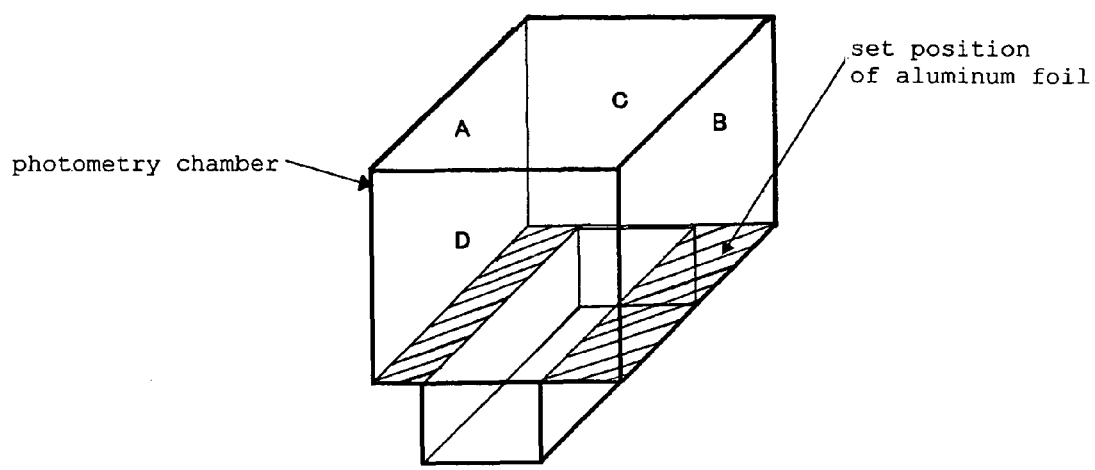
[FIG. 2] A view showing the frame format of the photometry chamber of SphereLight 180 which is automated chemiluminescence enzyme immunoassay analyzer used in Example 3.

What is claimed is:

1. A method for measuring an amount of an optically detectable compound to be measured in a sample, which comprises:

preventing an electric charge in an atmosphere in a photometry chamber from transferring to the surface of a solution which generates light due to an energy variation of a substance induced by the optically detectable compound in the sample, measuring value of the light, and determining an amount of the optically detectable compound in the sample on the basis of the measured value thus obtained, wherein the preventing step includes a step of making an atmosphere surrounding a reaction vessel and/or an atmosphere surrounding the reaction vessel in the photometry chamber electrically constant by using one or more of the following selected from the group consisting of:

(1) gas having a constant electric charge,
(2) a neutralization apparatus, or
(3) a material having a static electricity elimination effect.

2. The method according to claim 1, wherein the step of making the atmosphere surrounding the reaction vessel and/or the atmosphere surrounding the reaction vessel in the photometry chamber electrically constant includes attaching a material having a static electricity elimination effect on to an inside wall surface of the photometry chamber.

3. The method according to claim 1, wherein the step of making the atmosphere surrounding the reaction vessel and/or the atmosphere surrounding the reaction vessel in the photometry chamber electrically constant includes treating the atmosphere surrounding the reaction vessel at a stage before the reaction vessel is moved to the photometry chamber, by using one or more of the following selected from the group consisting of:

(1) gas having a constant electric charge,
(2) a neutralization apparatus, or
(3) a material having a static electricity elimination effect.

4. The method according to claim 1, wherein the light generated due to the energy variation of the substance is luminescence, fluorescence, or phosphorescence, which is induced by the presence of the optically detectable compound in the sample.

5. The method according to claim 1, wherein the step of making the atmosphere surrounding the reaction vessel and/or the atmosphere surrounding the reaction vessel in the photometry chamber constant includes treating the atmosphere surrounding the reaction vessel and/or the atmosphere surrounding the reaction vessel in the photometry chamber by using two or more of the following selected from the group consisting of:

(1) gas having a constant electric charge,
(2) a neutralization apparatus, or
(3) a material having a static electricity elimination effect.

6. The method according to claim 1, wherein the optically detectable compound is derived from an objective compound, and the amount of the objective compound is able to be determined by using a calibration curve showing a relationship between a concentration of the objective compound and a measured value which is previously obtained by measuring a standard solution containing a known amount of the objective component.

* * * * *